(12) United States Patent
Easley et al.

(10) Patent No.: US 10,660,793 B2
(45) Date of Patent: May 26, 2020

(54) MEDICAL DEVICE AND METHODS OF MANUFACTURING THEREOF

(71) Applicant: Vortex Surgical, Chesterfield, MO (US)

(72) Inventors: James C. Easley, Cottleville, MO (US); Douglas R. Parr, St. Peters, MO (US)

(73) Assignee: Vortex Surgical, Chesterfield, MO (US)

(*) Notice: Subject to any disclaimer, the term of this patent is extended or adjusted under 35 U.S.C. 154(b) by 261 days.

(21) Appl. No.: 15/672,614

(22) Filed: Aug. 9, 2017

(65) Prior Publication Data

US 2019/0046354 A1 Feb. 14, 2019

(51) Int. Cl.
| | | |
|---|---|---|
| *A61B 17/29* | (2006.01) | |
| *A61F 9/007* | (2006.01) | |
| *A61B 17/30* | (2006.01) | |
| A61B 17/28 | (2006.01) | |
| A61B 17/00 | (2006.01) | |

(52) U.S. Cl.
CPC ...... *A61F 9/00736* (2013.01); *A61B 17/2909* (2013.01); *A61B 17/30* (2013.01); *A61B 2017/00526* (2013.01); *A61B 2017/00867* (2013.01); *A61B 2017/00955* (2013.01); *A61B 2017/2825* (2013.01); *A61B 2017/2926* (2013.01); *A61B 2017/305* (2013.01)

(58) Field of Classification Search
CPC ......... A61B 17/28; A61B 17/29; A61B 17/30; A61B 17/282; A61B 17/2909; A61B 2017/2926; A61B 2017/0046; A61B 2017/305
See application file for complete search history.

(56) References Cited

U.S. PATENT DOCUMENTS

| | | | |
|---|---|---|---|
| 6,488,695 | B1 | 12/2002 | Hickingbotham |
| 6,908,476 | B2 | 6/2005 | Jud et al. |
| 6,945,984 | B2 | 9/2005 | Arumi et al. |
| 8,202,277 | B2 | 6/2012 | Ryan |
| 8,475,479 | B2 | 7/2013 | Linsi |
| 8,668,708 | B2 | 3/2014 | Linsi |
| 9,226,762 | B2 | 1/2016 | Scheller et al. |
| 2014/0128896 | A1 | 5/2014 | Ryan |
| 2015/0238355 | A1 | 8/2015 | Vessu et al. |
| 2016/0067091 | A1 | 3/2016 | Wells et al. |
| 2016/0296246 | A1 | 10/2016 | Schaller |
| 2016/0346107 | A1* | 12/2016 | Matthison-Hansen ...... A61B 17/30 |

FOREIGN PATENT DOCUMENTS

WO 2017053832 A1 3/2017

\* cited by examiner

*Primary Examiner* — Vi X Nguyen
(74) *Attorney, Agent, or Firm* — Armstrong Teasdale LLP

(57) ABSTRACT

The present disclosure is directed to medical devices and methods of manufacturing medical devices, such as an ophthalmologic medical device.

11 Claims, 5 Drawing Sheets

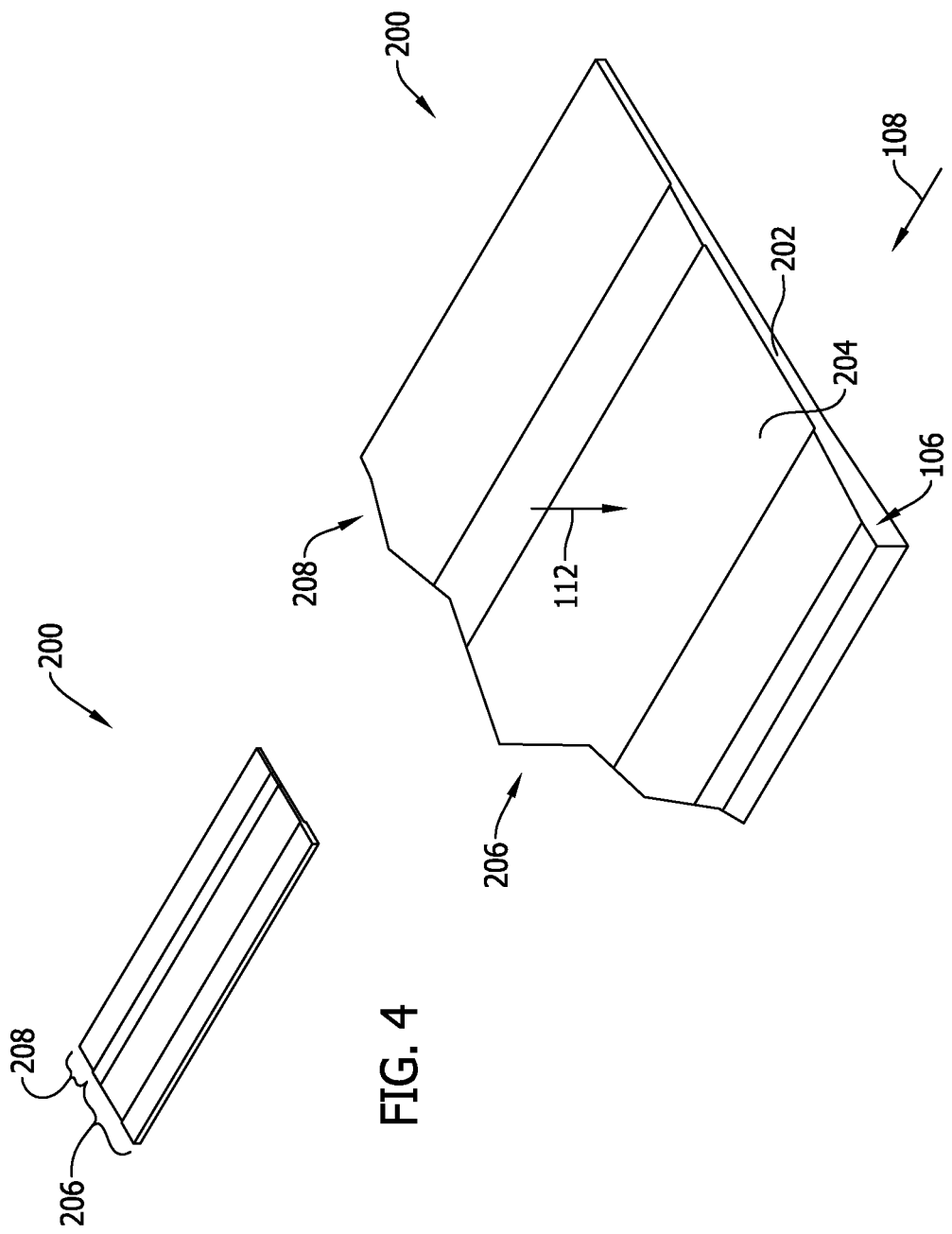

MEDICAL DEVICE AND METHODS OF MANUFACTURING THEREOF

BACKGROUND

The field of the disclosure relates generally to medical devices, and more specifically, to methods of manufacturing medical devices.

Many micro instruments that are intended to grasp or cut tissue share a common method of actuation. Generally, an elongate tube forms the outer portion of the operationally functional portion of the instrument. A rod or wire generally is enclosed by the elongate tube. Both members share a common axis. A handle, which takes many forms depending on the application, is attached to both the rod and tube. Actuation of the actuating mechanism in the handle causes relative motion of the rod and tube. In many instances, the relative motion is lengthwise along the common axis but in some instances the motion is radial around the common axis. In many instruments that are designed for grasping tissue, a distal portion of the rod is split axially forming two arms. The arms are formed so that they are biased away from each other and the central axis of the instrument when they are in a relaxed state. A grasping surface is formed on the end of each arm. In operation, the axial motion of the tube relative to the rod causes the tube to either allow the arms to relax and open the grasping surfaces away from each other or restrain the arms and cause the grasping surfaces to come together.

Manufacturing of the rod, arms, and grasping surface has conventionally been accomplished using several methods with limited success in meeting both precision and cost goals. One method includes machining, from a blank, the rod with a block on one end as a single piece. Subsequent operations using a wire electric discharge machine cuts the shape of the grasping surface and a split along the rod to form the arms. The rod is rotated and additional operations of the electric discharge machine are performed to form the complex shape of the grasping surface. Such manufacturing methods have limitations, especially as the desired size of the rod and grasping surfaces are decreased. Variation in the straightness of the rod, especially if heat treated, can cause undesirable geometric defects in the completed part. Also, the part is fabricated in the nearly closed position. This requires an additional operation to bend the arms in their biased outward relaxed position leaving an additional opportunity for geometric defect. If the arms aren't bent symmetrically enough, then the grasping surfaces on either arm don't align well when the arms are brought together.

Additionally, misalignment of the instrument blank within the machining device may result in the axis of the instrument arms not being on the same axis as the rod. Misalignment of a side profile of the instrument results in the instrument head, which include the arms, being offset from the axis of the actuation tube. Misalignment of a top profile of the instrument results in the arms not being symmetrical. An offset head can cause some features of the instrument to not be fully formed, and asymmetrical arms cause an imbalance in the actuation force and path of travel when the instrument is actuated. Such imbalance can cause undesired motions of the tip rather than a simple closure of the grasping surfaces on actuation. When a plurality of blanks are machined simultaneously, the results of misalignment of the instrument blank in the machine worsen because each blank's misalignment will be slightly different from each other blank, thus making repair very difficult.

BRIEF DESCRIPTION

In one aspect of the present disclosure, a method of manufacturing a medical device is provided. The method includes forming at least one sheet of material including a first surface and a second surface. The method also includes forming a first profile of a plurality of device heads in the first surface. The first profile is formed in a first orientation plane. The method further includes forming a second profile of the plurality of device heads in the second surface. The second profile is formed in a second orientation plane, and the plurality of device heads are entirely formed by the first profile and the second profile.

In another aspect of the present disclosure, a medical device is provided. The medical device includes a device head including a first arm having a first end and an opposing second end. The device head also includes a second arm having a third end and a fourth end. The first end is coupled to the third end, and the second end is spaced from the fourth end to define a gap therebetween. Each arm includes a pair of side surfaces and a pair of end surfaces. The side surfaces are defined by forming a first profile in a sheet of material in a first orientation plane, and the end surfaces are defined by forming a second profile in the sheet of material in a second orientation plane such that each arm is entirely defined by the first profile and the second profile.

BRIEF DESCRIPTION OF THE DRAWINGS

FIG. 4 is an exemplary embodiment of a perspective view of a sheet of material from which the medical device shown in FIG. 1 is formed in accordance with the present disclosure.

FIG. 5 is an exemplary embodiment of an enlarged view of a portion of the sheet of material shown in FIG. 4 in accordance with the present disclosure.

Although specific features of various embodiments may be shown in some drawings and not in others, this is for convenience only. Any feature of any drawing may be referenced and/or claimed in combination with any feature of any other drawing.

DETAILED DESCRIPTION

The present disclosure is directed to medical devices and methods of manufacturing medical devices. The examples described herein include a medical device and a method of manufacturing the same that includes only two steps to form the device. More specifically, a first profile is formed in a first surface of a sheet of material in a first orientation plane, and a second profile is formed in a second surface of the sheet of material in a second orientation plane. Forming the first and second profiles results in the complete formation of a device head including a pair of arms and at least a portion of a rod. Once the second profile is formed, the device heads are removed from sheet and ready for any desired post-machining processing. Such a two-step manufacturing method is advantageous not only due to a faster machining time and lower expense, but also because the described method is tolerant of the position of sheet of material within the manufacturing equipment. Additionally, the arms of the device head are formed in the open position, so a subsequent machining step to bend the arms out into the open position is not required.

In some embodiments of the present disclosure, the medical device includes an ophthalmologic device, an optometric device, a probe, a vitrectomy device, a microsurgical device, an endoscopic surgical device, a neurosurgical device, or a plastic surgical device. In some embodiments, the medical device is used an as instrument, such as a microsurgical instrument, in an operation (e.g., surgery) conducted in or around an eye. The device is used, for example, in surgical treatment of retinal diseases, as for example resulting from hypertonia, or other vascular changes.

Figure 1:
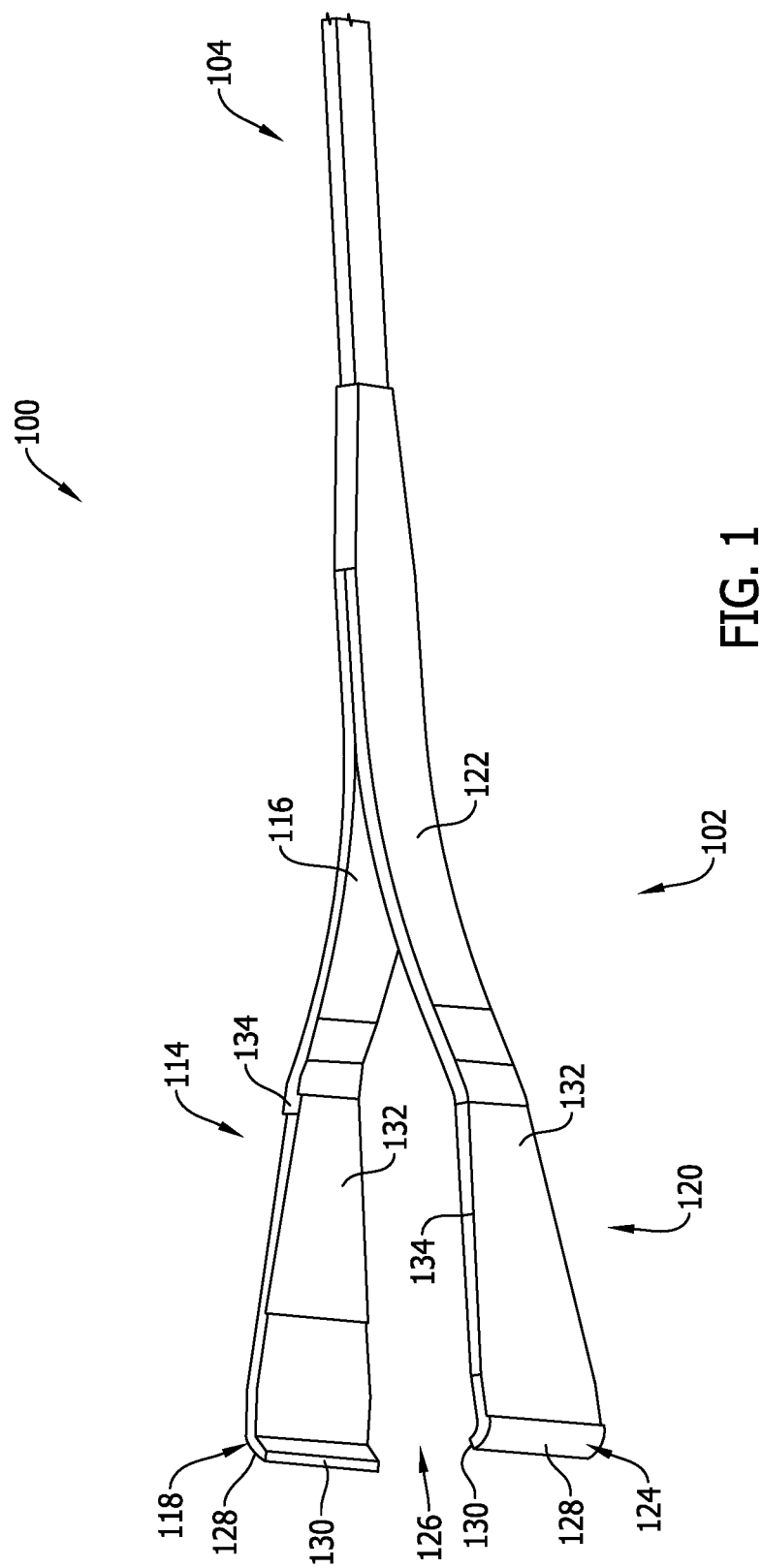
FIG. 1 is a perspective view of an exemplary medical device illustrating a device head and a portion of a rod in accordance with the present disclosure.
Figure 2:
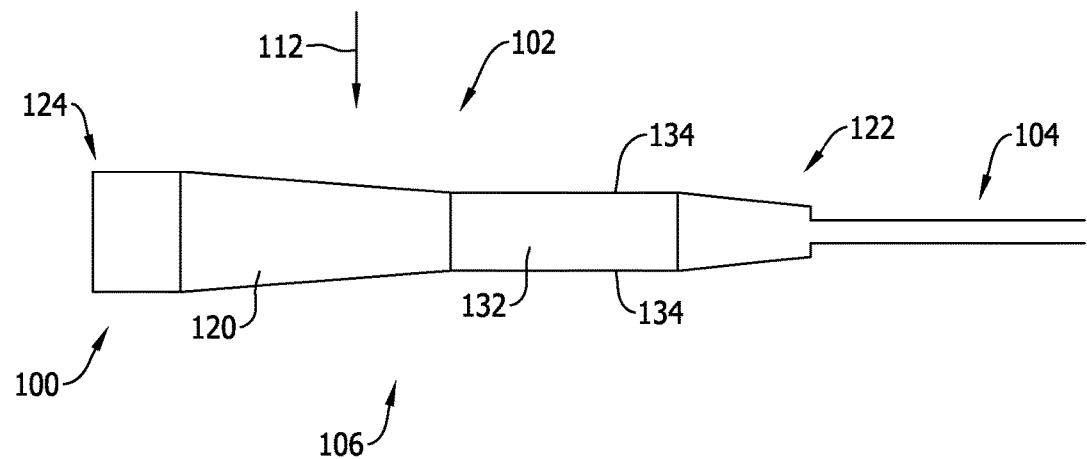
FIG. 2 is an exemplary embodiment of a side view of the device head shown in FIG. 1 illustrating a first profile of the device head from a first orientation plane in accordance with the present disclosure.
Figure 3:
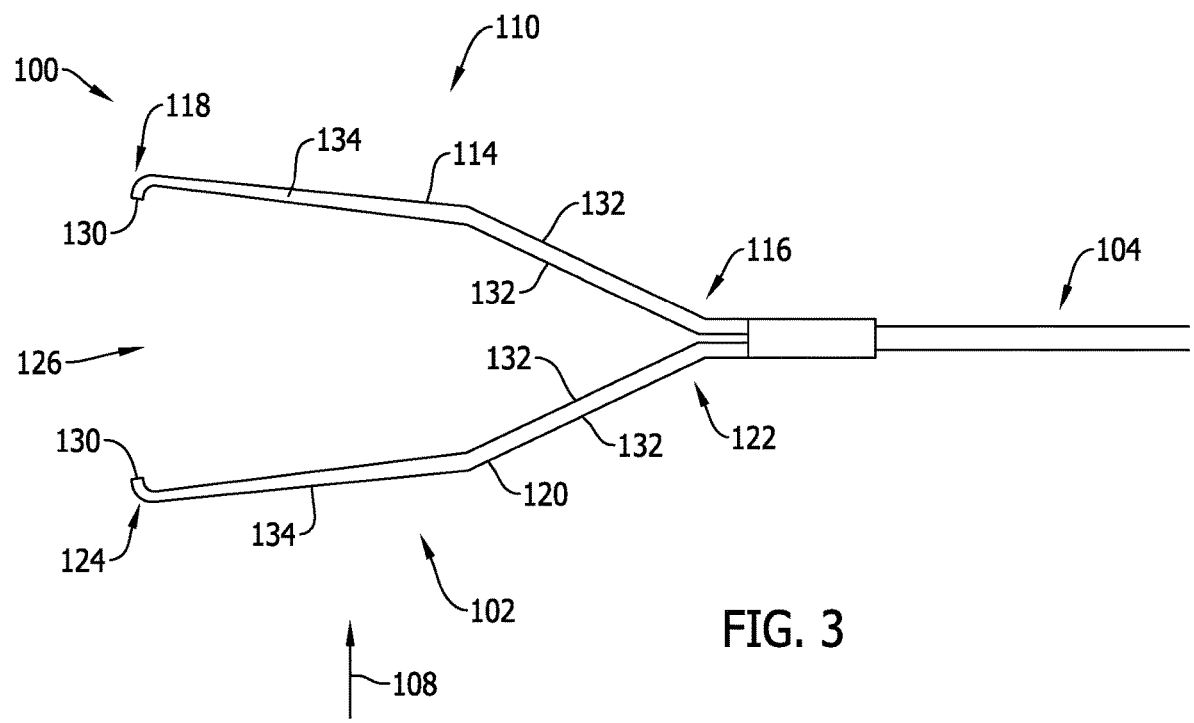
FIG. 3 is an exemplary embodiment of a top view of the device head shown in FIG. 1 illustrating a second profile of the device head from a second orientation plane in accordance with the present disclosure.

FIG. 1 is a perspective view of an exemplary medical device 100 including a device head 102 and a portion of a rod 104. FIG. 2 is a side view of device head 102 and rod 104 illustrating a side or first profile 106 of device head 102 as seen from a first orientation plane 108 (shown in FIG. 3). FIG. 3 is a top view of device head 102 and rod 104 illustrating a top or second profile 110 of device head 102 as seen from a second orientation plane 112 (shown in FIG. 2).

In the exemplary embodiment, device 100 is formed from any of a variety of materials. More specifically, device 100 is formed from a medical grade material. For example, device 100 is formed from a metal, such as titanium or stainless steel, nickel-titanium alloys or "Nitinol," or other similar alloy materials. In embodiments where device 100 is formed from stainless steel, device 100 is formed from any of 20 gauge, 23 gauge, 25 gauge, 27 gauge stainless steel and combinations thereof. Alternatively, device 100 is formed from a polymer, such as a medical grade plastic; synthetic materials (e.g., synthetic fibers or synthetic diamond); thermoplastic materials; or composite materials. In some embodiments, device 100 is an instrument that is disposable after a single use. In some embodiments, device 100 is reusable, and in some embodiments sterilizable.

In the exemplary embodiment, rod 104 is coupled to head 102. More specifically, in one embodiment, rod 104 is integrally formed with head 102. In another embodiment, rod 104 is formed separately from head 102 and is coupled to head 102 using at least one of laser welding, crimping, at least one adhesive, and corresponding threaded surfaces.

Head 102 includes a first arm 114 having a first end 116 located proximate rod 104 and a distal second end 118. Similarly, head 102 also includes a second arm 120 having a third end 122 located proximate rod 104 and a distal fourth end 124. First end 116 of first arm 114 is coupled to third end 122 of second arm 120, and second end 118 of first arm 114 is spaced from fourth end 124 of second arm 120 to define a gap 126 therebetween when device 100 is in an open position.

In the exemplary embodiment, second and fourth ends 118 and 124 each include a curved portion 128 defining a hooked or C-shaped configuration that each include a gripping surface 130. The curved nature of curved portion 128 permits gripping surfaces 130 to be offset inwardly from the remainder of arms 114 and 120. Furthermore, gripping surfaces 130 are aligned with each other so as to substantially engage when arms 114 and 120 are moved into the closed position. As described herein, gripping surfaces 130 are defined by the second profile 110 in the second orientation plane 112.

As shown in FIGS. 1-3, each arm 114 and 120 includes a pair of side surfaces 132 and a pair of end surfaces 134. As described herein, side surfaces 132 are defined by forming first profile 106 (shown in FIG. 2) in a sheet of material in the first orientation plane 108, and end surfaces 134 are defined by forming second profile 110 in the sheet of material in the second orientation plane 112. In the exemplary embodiment, each arm 114 and 120, and therefore head 102, is entirely defined by first profile 106 and second profile 110.

In the exemplary embodiment, side surfaces 132 of each arm 114 and 120 are oriented perpendicular to end surfaces 134 of each arm 114 and 120. In such a configuration, the first orientation plane 108 is oriented perpendicular to the second orientation plane 112. Alternatively, side surfaces 132 and end surfaces 134 are obliquely oriented with respect to each other. In such a configuration, the first orientation plane 108 is obliquely oriented with respect to the second orientation plane 112.

As best shown in FIG. 2, in the exemplary embodiment, side surfaces 132 include a varying thickness between opposing end surfaces 134 based on a position between ends 116 and 118 of first arm 114 and between ends 122 and 124 of second arm 120. Because the thickness of end surfaces 134 between side surfaces 132 changes along the length of arms 114 and 120, end surfaces 134 include a varying thickness in the second orientation plane 112. As shown in FIG. 2, along their lengths, end surfaces 134 include portions of constant thickness and portions of varying thickness between side surfaces 132, such that, overall, end surfaces 134 include a varying thickness. Alternatively, end surfaces 134 include a constant thickness defined between side surfaces 132 along their lengths between ends 116 and 118 of first arm 114 and between ends 122 and 124 of second arm 120.

Similarly, as best shown in FIG. 3, in the exemplary embodiment, end surfaces 134 of arms 114 and 120 also include a varying thickness between opposing side surfaces 132 based on a position between ends 116 and 118 of first arm 114 ends 122 and 124. Although described herein with respect to second arm 120, first arm 114 is substantially similar to second arm 120 and includes the same features described herein with respect to second arm 120. Because the thickness of side surfaces 132 changes along the length of second arm 120, side surfaces 132 include a varying thickness in the first orientation plane 108. As shown in FIG. 2, along their lengths, side surfaces 132 include portions of constant thickness and portions of varying thickness between end surfaces 134, such that, overall, side surfaces 132 include a varying thickness. Alternatively, side surfaces 132 include a constant thickness defined between end surfaces 134 along their lengths between ends 122 and 124.

Figure 6:
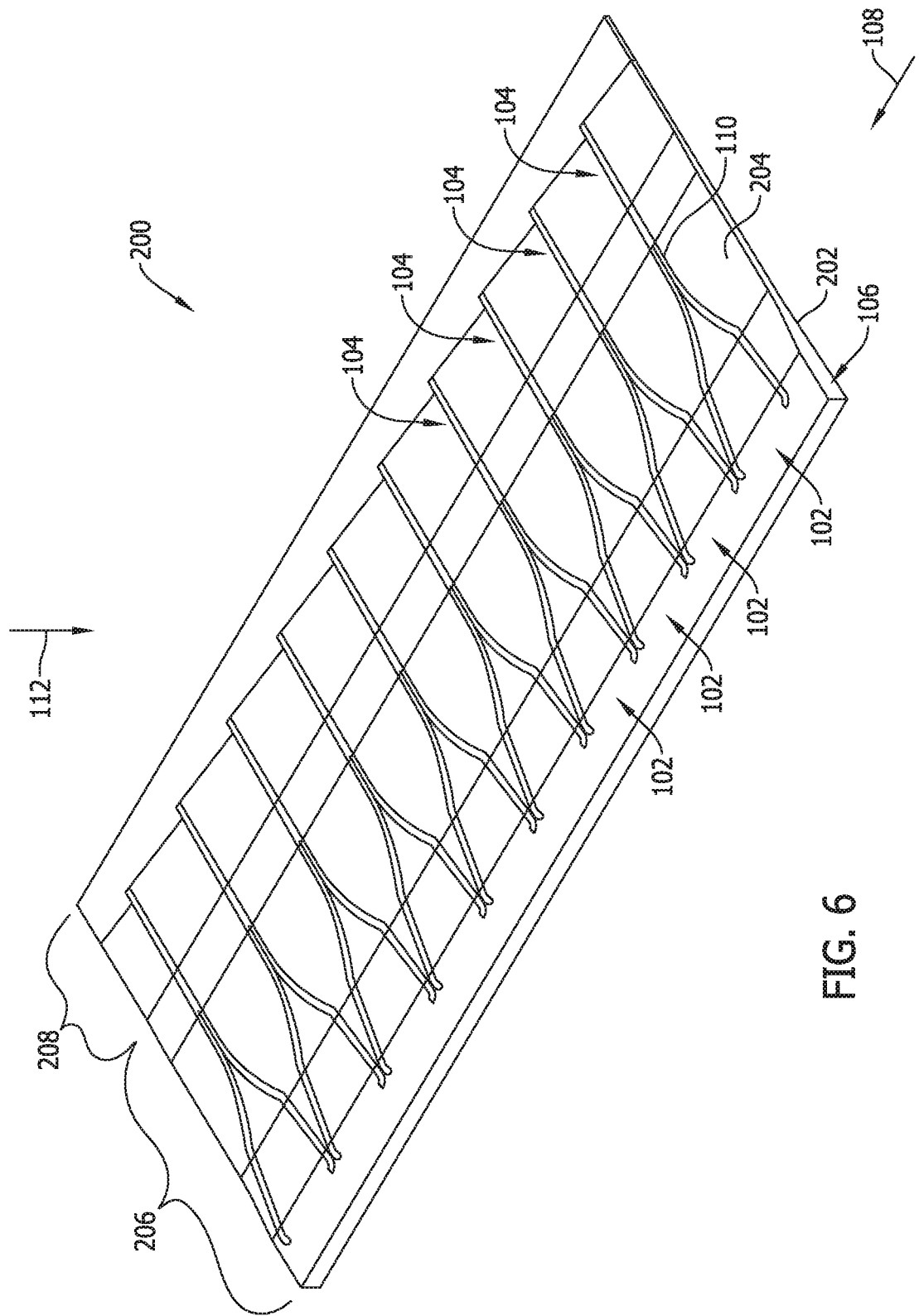
FIG. 6 is an exemplary embodiment of a perspective view of the sheet of material shown in FIG. 4 with a plurality of device heads formed therein in accordance with the present disclosure.

FIG. 4 is a perspective view of a sheet of material 200 from which medical device 100 is formed. FIG. 5 is an enlarged view of a portion of sheet of material 200 illustrating the first profile 106 of head 102 (shown in FIGS. 1-3), and FIG. 6 is a perspective view of sheet of material 200 illustrating a plurality of second profiles 110 of device heads 102 formed therein.

As described above, sheet 200 is formed from a metal, such as titanium or stainless steel, nickel-titanium alloys or "Nitinol," or other similar alloy materials. In embodiments where sheet 200 is formed from stainless steel, sheet 200 is formed from any of 20 gauge, 23 gauge, 25 gauge, 27 gauge stainless steel and combinations thereof. Alternatively, sheet 200 is formed from a polymer, such as a medical grade plastic; synthetic materials (e.g., synthetic fibers or synthetic diamond); thermoplastic materials; or composite materials.

In the exemplary embodiment, material sheet 200 begins the manufacturing process as a sheet having a constant thickness. In order to manufacture device 100, sheet 200 is machined to form the first profile 106 in a side or first surface 202 of sheet 200 and to form second profile in a top or second surface 204 of sheet 200. In the exemplary embodiment, first surface 202 is oriented perpendicular to second surface 204. In such a configuration, the first orientation plane 108 is oriented perpendicular to the second orientation plane 112. Alternatively, surfaces 202 and 204 are obliquely oriented with respect to each other. In such a configuration, the first orientation plane 108 is obliquely oriented with respect to the second orientation plane 112.

In the exemplary embodiment, the first profile 106 of a plurality of device heads 102 is formed in first surface 202 such that the first profile 106 is formed in the first orientation plane 108. More specifically, forming the first profile 106 in first surface 202 includes forming a side profile of the plurality of device heads 102 in first surface 202. As described herein, forming the first or side profile 106 incudes forming a first or side profile with a varying thickness in first surface 202. In the exemplary embodiment, first profile 106 is formed in first surface 202 of sheet 200 by electric discharge machining (EDM). Alternatively, first profile 106 is formed in first surface 202 of sheet 200 using, alone or in any combination, EDM, roll forming, stamping, extruding, and laser cutting.

After the first profile 106 is formed, sheet 200 includes a head portion 206 and a rod portion 208. As described herein, a plurality of device heads 102 will be formed in head portion 206 of sheet 200 and a plurality of rods 104 will also be formed in rod portion 208 of sheet 200. Once the first profile 106 is formed in first surface 202, then the second profile 110 of the plurality of heads 102 is formed in second surface 204 to define rod 104, arms 114 and 120, and gripping surfaces 130 in second surface 204. As described herein, forming the second profile 110 incudes forming arms 114 and 120 that include a varying thickness in second surface 204. Additionally, arms 114 and 120 are formed in the open position such that a bending step is not required to place arms 114 and 120 in the open position. Similar to forming the first profile 106, the second profile 110 is formed in second surface 204 of sheet 200 by electric discharge machining (EDM). Alternatively, second profile 110 is formed in second surface 204 of sheet 200 using, alone or in any combination, EDM, stamping, extruding, and laser cutting.

As the first profile 106 is formed in the first orientation plane 108, the second profile 110 is formed in the second orientation plane 112, such that the plurality of device heads 102 are entirely formed by the first profile 106 and the second profile 110. More specifically, device heads 102 are completely formed by only two machining steps; the first step being forming the first profile 106 in the first surface 202 and the second step being forming the second profile 110 in the second surface 204. Once the second profile 110 is formed, the device heads 102 are removed from sheet 200 and ready for any desired post-machining processing. Such a manufacturing method is advantageous not only due to a faster machining time and lower expense, but also because the described method is tolerant of the position of sheet 200 within the manufacturing equipment.

In the exemplary embodiment, forming the first and second profiles 106 and 110 in sheet 200 includes coupling a plurality of rods 104 to the plurality of device heads 102 in a one-to-one relationship such that each rod 104 is coupled to a single respective device head 102 of the plurality of device heads 102. As shown in FIG. 6, at least a portion of rod 104 is integrally formed with a respective device head 102 on sheet 200. In alternative embodiments, rods 104 are formed separate from device heads 102 and subsequently coupled to a respective device head 102. In such embodiments, each rod 104 is coupled to a respective device head 102 using at least one of laser welding, crimping, at least one adhesive, and corresponding threaded surfaces. In the exemplary embodiment, a portion of rod 104 is integrally formed with device heads and a separate rod extension (not shown) is coupled to rod 104 to form device 100. Alternatively, sheet 200 is sized such that an entirety of rod 104 is formed in sheet 200.

Figure 7:
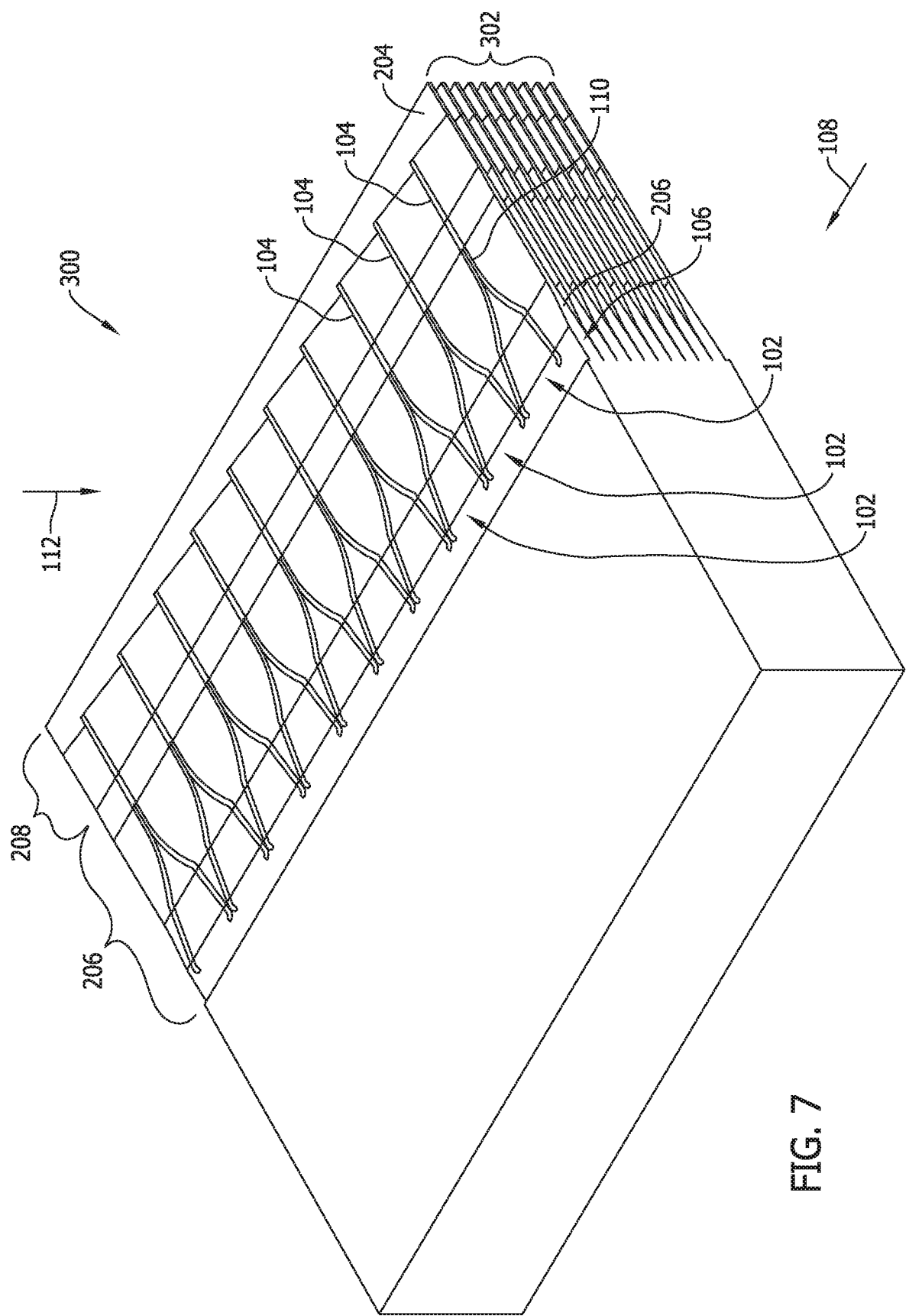
FIG. 7 is an exemplary embodiment of a perspective view of a block of material illustrating a plurality of sheets of material that each include a plurality of device heads formed therein in accordance with the present disclosure.

FIG. 7 is a perspective view of a block 300 of material illustrating a plurality of sheets 302 of material that each include a plurality of device heads 102 and rods 104 formed therein. Each sheet 302 is substantially similar in configuration as sheet 200 shown in FIGS. 4-6. As such, like elements in sheets 302 and sheet 200 are identified by like reference numerals in FIG. 7. Material block 300 is identical to sheet 200 in composition with the exception that block 300 is substantially thicker than sheet 200. As such, a plurality of sheets 302 are able to be formed into block 300. As shown in FIG. 7, sheets 302 are coupled together such that alignment of sheets 302 is maintained during formation of device heads 102 and rods 104. More specifically, sheets 302 are integrally formed together at an edge proximate gripping surfaces 130 of arms 114 and 120. Alternatively, sheets 302 are not integrally formed and are separate sheets 200 stacked together. As described herein, the positional tolerance of the described methods enables stacking of sheets 302 to allow forming a plurality of heads 102 and rods 104 within required dimensions.

In such a configuration, forming the first profile 106 in first surface 202 includes forming the first profile 106 in each of the plurality of first surfaces 202 of sheets 302. Similarly, forming the second profile 110 in second surface 204 includes forming the second profile 110 in each of the plurality of second surfaces 204 of sheets 302.

As described above, forming the device 100 from only two profiles is more tolerant to misalignment of block 300 in the manufacturing machine. For example, in an EDM manufacturing machine, if a Y axis is defined as the longitudinal axis of instrument 100 along rod 104, then any position misalignment of material block 300 in the machine is compensated for by the machine. Known wire EDM machines can determine when the wire contacts material block 300. When a plurality of first profiles 106 are cut from material block 300 then any Y axis misalignment is the same for all of the first profiles 106 and any compensation by the wire EDM machine is effective for all of the first profiles 106, yielding the exact desired shape for all profiles. Misalignment in the X axis, the direction of first orientation plane 108, has no effect on the shape of head 102 since the second profile 110 is simply shifted sideways on the sheet 302 that has already been formed with the first profile 106 and no defect is caused. Misalignment of device head 102 and rod 104 is not possible using the method described herein since at least part of rod 104 is formed simultaneous to forming device head 102. Although described above with respect to material block 300, the method described herein is also tolerant to misalignment of individual sheets 200 within the manufacturing machine.

Additional technical effects of the above-described manufacturing method results in consistent geometry of the device heads, which provides for more consistent performance for the user and lower scrap costs for the manufacturer. Moreover, a larger number of tips can be produced simultaneously, further reducing cost because the effective machine time per device head is reduced.

Exemplary embodiments of the medical device are described above in detail. The medical device and its manufacturing methods are not limited to the specific embodiments described herein, but rather, components of the device may be utilized independently and separately from other components described herein. For example, the components may also be used in combination with other medical devices and systems, methods, and apparatuses, and are not limited to practice with only the systems and methods as described herein. Rather, the exemplary embodiments can be implemented and utilized in connection with many other applications.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the disclosure, including the best mode, and to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of manufacturing a medical device, said method comprising:
   forming at least one sheet of material, wherein the at least one sheet of material includes a first surface and a second surface;
   forming a first profile of a plurality of device heads in the first surface, wherein the first profile is formed in a first orientation plane; and,
   forming a second profile of the plurality of device heads in the second surface, wherein the second profile is different from the first profile, wherein the second profile is formed in a second orientation plane, wherein the plurality of device heads are entirely formed by the first profile and the second profile.

2. The method in accordance with claim 1, further comprising coupling a plurality of rods to the plurality of device heads in a one-to-one relationship such that each rod of the plurality of rods is coupled to a single device head of the plurality of device heads.

3. The method in accordance with claim 1, wherein the first surface is oriented perpendicular to the second surface.

4. The method in accordance with claim 1, wherein forming the at least one sheet of material comprises forming a plurality of sheets of material, and wherein forming the first profile in the first surface comprises forming the first profile in the first surface of each of the plurality of sheets of material.

5. The method in accordance with claim 1, further comprising forming a block of material, wherein forming the at least one sheet of material comprises forming a plurality of sheets of material from the block of material, wherein the plurality of sheets are integrally coupled together.

6. The method in accordance with claim 1, wherein forming the first profile in the first surface includes forming a side profile of the plurality of device heads in the first surface.

7. The method in accordance with claim 1, wherein forming the second profile in the second surface includes forming a rod portion, a pair of arms, and a gripping surface on each arm in the second surface.

8. The method in accordance with claim 1, wherein forming the first profile includes forming the first profile using at least one of roll forming stamping, electric discharge machining (EDM), extruding, and laser cutting.

9. The method in accordance with claim 1, wherein forming the second profile comprises forming the second profile using at least one of stamping, electric discharge machining, and laser cutting.

10. The method in accordance with claim 1, wherein forming the sheet of material comprises forming the sheet of material from one of stainless steel, titanium, a nickel-titanium alloy, and thermoplastic materials.

11. The method in accordance with claim 1, wherein the medical device is selected from the group consisting of an ophthalmologic device, an optometric device, a microsurgical device, an endoscopic surgical device, a neurosurgical device, or a plastic surgical device.

* * * * *